(12) United States Patent
Oogami (10) Patent No.: US 7,986,767 B2
(45) Date of Patent: Jul. 26, 2011

(54) RADIOGRAPHIC IMAGE DETECTION APPARATUS

(75) Inventor: Satoru Oogami, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 98 days.

(21) Appl. No.: 12/588,348

(22) Filed: Oct. 13, 2009

(65) Prior Publication Data

US 2010/0094850 A1    Apr. 15, 2010

(30) Foreign Application Priority Data

Oct. 15, 2008   (JP) .................................. 2008-265971

(51) Int. Cl.
*H05G 1/30* (2006.01)
*H05G 1/08* (2006.01)

(52) U.S. Cl. ............ 378/62; 378/91; 378/165; 378/196; 378/197

(58) Field of Classification Search .................... 378/62, 378/91, 165, 189, 196, 197
See application file for complete search history.

(56) References Cited

U.S. PATENT DOCUMENTS

| 6,463,121 B1 * | 10/2002 | Milnes ............................ 378/62 |
| 6,895,076 B2 * | 5/2005 | Halsmer et al. ............. 378/98.12 |
| 7,623,622 B2 * | 11/2009 | Camus et al. .................... 378/62 |
| 7,639,782 B2 * | 12/2009 | Zelnik et al. .................... 378/62 |
| 7,643,612 B2 * | 1/2010 | Benndorf et al. ............... 378/98 |

FOREIGN PATENT DOCUMENTS

JP    11-244272    9/1999

* cited by examiner

*Primary Examiner* — Allen C. Ho
(74) *Attorney, Agent, or Firm* — Jean C. Edwards, Esq.; Edwards Neils PLLC (57) ABSTRACT

An actual-past-radiography position database stores, as actual-past-radiography positions, the position of a radiographic image detector and the position of a radiation source when radiography was actually performed, associating the position of the radiographic image detector and the position of the radiation source with information about a subject. When the radiation source and the radiographic image detector are positioned to perform radiography, position adjustment amounts for adjusting the positions of the radiation source and the radiographic image detector from standard positions stored in the standard position database are output, as aid information. The aid information is output based on the actual-past-radiography positions that are stored in the actual-past-radiography position database and that are associated with the information about the subject.

5 Claims, 4 Drawing Sheets

RADIOGRAPHIC IMAGE DETECTION APPARATUS

CROSS-REFERENCE TO RELATED APPLICATIONS

The present application claims priority from Japanese Patent Application No. 2008-265971, filed Oct. 15, 2008, the contents of which are herein incorporated by reference in their entirety.

BACKGROUND OF THE INVENTION

1. Field of the Invention

The present invention relates to a radiographic image detection apparatus that obtains a plurality of radiographic images by changing the positions of a radiation source and a radiographic image detector and by irradiating a subject with radiation.

2. Description of the Related Art

Conventionally, radiography has been performed on a predetermined region of a patient to obtain radiographic images of the region from a plurality of angles (directions) so that the patient is diagnosed by using the obtained radiographic images. Especially, in medical diagnosis, the same region of the patient is radiographed periodically to observe the progress and the condition of the disease or the like in many cases. Therefore, it is desirable that the angle of radiography in each periodic radiography operation is the same as the angle of radiography performed on the same patient in the past. Meanwhile, the sex, the height and the like of every patient (a person to be examined or radiographed, a subject) differ from each other. Therefore, when radiography is performed, it is necessary to finely adjust the position of the radiation source and the position of the radiographic image detector for each patient.

Here, a method for positioning a radiation source and a radiographic image detector when radiography is periodically performed has been proposed (please refer to Japanese Unexamined Patent Publication No. 11(1999)-244272 (Patent Literature 1), for example). In the method, the positions in the past radiography are stored, and the stored positions are used to position the radiation source and the radiographic image detector when a periodic radiography operation is performed. Specifically, in Patent Literature 1, the order of radiography and the position of the radiographic image detector or the like are stored in a header of a radiographic image obtained by radiography. When radiography is performed next time, the stored information is read out from the header of the radiographic image, and the radiographic image detector or the like is positioned.

In Patent Literature 1, efficient radiography may be performed on a patient who was radiographed in the past. However, when a patient is radiographed for the first time, an operator (a radiographer, a radiological technician, or the like) needs to adjust the position of the radiation source and the position of the radiographic image detector. Even when radiography is performed on the patient for the first time, it is desirable that the radiation source and the radiographic image detector are positioned in a short time period to perform efficient radiography.

SUMMARY OF THE INVENTION

In view of the foregoing circumstances, it is an object of the present invention to provide a radiographic image detection apparatus that can position a radiation source and a radiographic image detector in a short time period to perform efficient radiography.

A radiographic image detection apparatus of the present invention is a radiographic image detection apparatus comprising:

a radiation source that outputs radiation to a subject;

a radiographic image detector that detects, as a radiographic image, the radiation that has been output from the radiation source to the subject and that has passed through the subject;

a detector movement means that moves the position of the radiographic image detector;

a radiation-source movement means that moves the position of the radiation source;

a standard position database that stores, in advance, a standard position of the radiographic image detector and a standard position of the radiation source for obtaining the radiographic image by changing the position of the radiographic image detector and the position of the radiation source;

an actual-past-radiography position database that stores, as actual-past-radiography positions, the position of the radiographic image detector and the position of the radiation source when radiography was actually performed, associating the position of the radiographic image detector and the position of the radiation source with information about the subject; and an aid-information output means that outputs, as aid information, position adjustment amounts for adjusting the positions of the radiation source and the radiographic image detector from the standard positions stored in the standard position database when the radiation source and the radiographic image detector are positioned to perform radiography, wherein the aid information is output based on the actual-past-radiography positions that are stored in the actual-past-radiography position database and that are associated with the information about the subject.

The type of the radiographic image detector is not limited as long as the radiographic image detector detects, as a radiographic image, radiation that has passed through a subject. For example, the radiographic image detector may be a so-called TFT (thin-film transistor) type radiographic image detector. Alternatively, the radiographic image detector may be a so-called light-readout-type radiographic image detector.

Further, the information about the subject may be the name or the sex of the subject, or the like. Further, the information about the subject may include a physical characteristic of the subject, such as the height and the weight of the patient. Alternatively, the information about the subject may be an electronic clinical chart (medical sheet) of the subject that includes the condition of the subject (patient), the content of diagnosis, or the like.

Further, the standard positions and the actual-past-radiography positions may include at least one of the position or the angle of the radiation source, the collimator rotation angle or the irradiation field of the irradiation source, and the position or the angle of the radiographic image detector.

The structure of the aid-information output means is not limited as long as the aid-information output means outputs the position information amount as the aid information. For example, the aid-information output means may include an information classification means, an aid-information generation means, and an aid-information retrieval means. The information classification means may classify the actual-past-radiography positions stored in the actual-past-radiography position database for each physical characteristic of the subject. The aid-information generation means may generate, as the aid information, an average value or a mode value of the actual-past-radiography positions for each physical characteristic classified by the information classification means. The aid-information retrieval means may retrieve the aid information about a classification group to which the subject to be radiographed belongs from a plurality of sets of aid information generated by the aid-information generation means, and output the retrieved aid information.

The actual-past-radiography position database may store information about an operator who performed radiography and the order (sequence) of radiography performed by the operator, associating the information about the operator and the order of radiography with the actual-past-radiography positions. At this time, the aid-information output means may calculate an average value of time periods for radiography by each operator, and output, as the aid information, the order of radiography performed by the operator who has a lowest average value of time periods.

Further, the radiographic image detection apparatus may further include a radiography control means that controls the detector movement means and the radiation-source movement means so that the radiation source and the radiographic image detector are positioned as indicated by the actual-past-radiography-positions of the subject to be radiographed when the actual-past-radiography-positions of the subject to be radiographed are stored in the actual-past-radiography position database.

A radiographic image detection apparatus of the present invention includes:

a radiation source that outputs radiation to a subject;

a radiographic image detector that detects, as a radiographic image, the radiation that has been output from the radiation source to the subject and that has passed through the subject;

a detector movement means that moves the position of the radiographic image detector;

a radiation-source movement means that moves the position of the radiation source;

a standard position database that stores, in advance, a standard position of the radiographic image detector and a standard position of the radiation source for obtaining a plurality of radiographic images by changing the position of the radiographic image detector and the position of the radiation source;

an actual-past-radiography position database that stores, as actual-past-radiography positions, the position of the radiographic image detector and the position of the radiation source when radiography was actually performed, associating the position of the radiographic image detector and the position of the radiation source with information about the subject; and an aid-information output means that outputs, as aid information, position adjustment amounts for adjusting the positions of the radiation source and the radiographic image detector from the standard positions stored in the standard position database when the radiation source and the radiographic image detector are positioned to perform radiography. Further, the aid information is output based on the actual-past-radiography positions that are stored in the actual-past-radiography position database and that are associated with the information about the subject. Therefore, when radiography is performed on a subject, even if position data on the subject is not recorded in the actual-past-radiography position database, it is possible to provide aid information, as an index for positioning the radiation source and the radiographic image detector, for the operator. Hence, the operator can position the radiation source and the radiographic image detector in a short time period to perform efficient radiography.

When the information about the subject is a physical characteristic of the subject, and when the aid-information output means includes an information classification means, an aid-information generation means, and an aid-information retrieval means, it is possible to provide useful aid information that is based on the physique (physical type, or the like) of the subject for the operator. Here, the information classification means may classify the actual-past-radiography positions stored in the actual-past-radiography position database for each physical characteristic of the subject. The aid-information generation means may generate, as the aid information, an average value or a mode value of the actual-past-radiography positions for each physical characteristic classified by the information classification means. The aid-information retrieval means may retrieve the aid information about a classification group to which the subject to be radiographed belongs from a plurality of sets of aid information generated by the aid-information generation means, and outputs the retrieved aid information.

When the actual-past-radiography position database stores information about an operator who performed radiography and the order of radiography performed by the operator, associating the information about the operator and the order of radiography with the actual-past-radiography positions, and the aid-information output means calculates an average value of time periods for radiography by each operator, and outputs, as the aid information, the order of radiography performed by the operator who has a lowest average value of time periods, it is possible to perform the operation of positioning the radiation source and the radiographic image detector with reference to the radiography operation by the operator who performed radiography in the shortest time period. Therefore, efficient radiography is performed.

If the radiographic image detection apparatus further includes a radiography control means that controls the detector movement means and the radiation-source movement means so that the radiation source and the radiographic image detector are positioned as indicated by the actual-past-radiography-positions of the subject to be radiographed when the actual-past-radiography-positions of the subject to be radiographed are stored in the actual-past-radiography position database, the radiation source and the radiographic image detector can be moved to the same positions as the past radiography performed on the same subject. Hence, when radiography was performed on the same subject in the past, and the actual-past-radiography positions are stored, efficient radiography is possible to diagnose the subject by comparing the obtained radiographic images with the past radiographic images of the subject.

DESCRIPTION OF THE PREFERRED EMBODIMENTS

Figure 1:
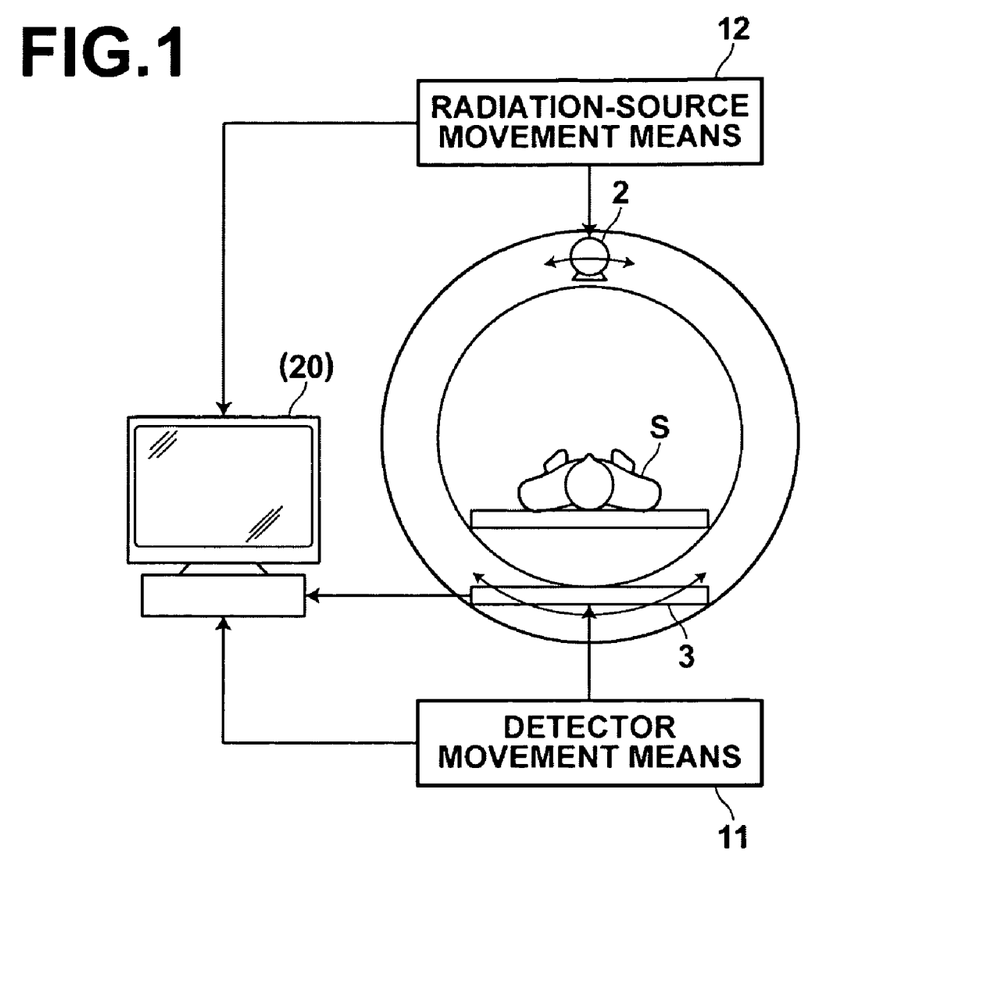
FIG. 1 is a schematic diagram illustrating an embodiment of a radiographic image detection apparatus of the present invention.
Figure 2:
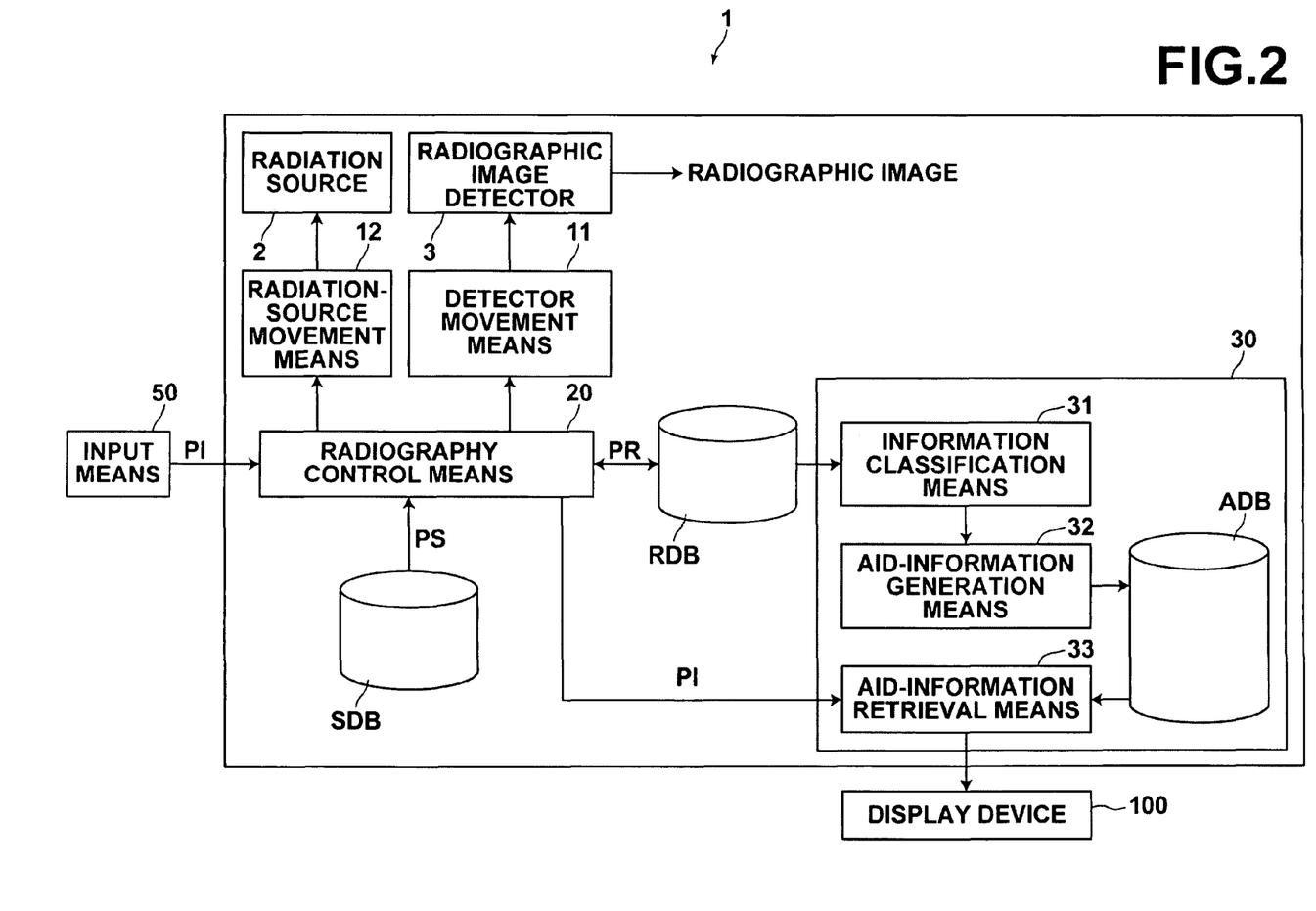
FIG. 2 is a block diagram illustrating an embodiment of a radiographic image detection apparatus of the present invention.

Hereinafter, embodiments of the present invention will be described with reference to drawings. FIG. 1 is a schematic diagram illustrating a side view of a radiographic image detection apparatus according to an embodiment of the present invention. FIG. 2 is a block diagram illustrating an embodiment of the radiographic image detection apparatus of the present invention. A radiographic image detection apparatus 1 is a so-called radiographic CT (computed tomography) apparatus, which performs radiography of a subject a plurality of times from different directions from each other.

The radiographic image detection apparatus 1 includes a radiation source 2, a radiographic image detector (radiation detector) 3, a detection movement means 11, a radiation source movement means 12, a radiography control means 20, and an aid-information output means 30. The radiation source 2 outputs radiation to subject S. The radiation source 2 is controlled by the radiography control means 20. The radiographic image detector 3 detects, as a radiographic image, distribution of the transmittance of radiation that has passed through the subject S. Specifically, the radiographic image detector 3 stores, as a static latent image, radiographic image information represented by radiation that has passed through the subject S, and reads out the stored static latent image to detect the radiographic image. The structure of the radiographic image detector 3 is not limited as long as the radiographic image detector 3 detects radiation and outputs the detected radiation as image information. For example, the radiographic image detector 3 may be a TFT-type solid-state detector. Alternatively, the radiographic image detector 3 may be a light-readout-type solid-state detector.

The detector movement means 11 moves the position of the radiographic image detector 3 relative to the subject S. For example, the detector movement means 11 includes a rail, a bearing, and a drive means, such as a motor. The radiation-source movement means 12 moves the position of the radiation source 2 based on the position of the radiographic image detector 3.

The radiography control means 20 controls the radiography operation of the radiographic image detection apparatus 1. The radiography control means 20 has a function of automatically correlating a region of the subject S with the position of the radiation source 2 and the position of the radiographic image detector 3 by using standard positions PS stored, in advance, in a standard position database SDB. The radiography control means 20 automatically correlates the region of the subject S based on information about a radiography range for the subject S and information about an actual radiography range. The radiography control means 20 controls each apparatus (unit) so that each radiography is performed at an optimum dose.

When the radiography control means 20 positions the radiation source 2 and the radiographic image detector 3 with respect to the subject S, if the radiation source 2 and the radiographic image detector 3 are positioned at standard positions PS, positioning may not be performed in a desirable manner. For example, the positions may not be appropriate for the physique of the subject S. In this case, the position of the radiation source 2 and the position of the radiographic image detector 3 are adjusted by an operator UI, and radiography is performed after the adjustment. The radiography control means 20 stores, as actual-past-radiography positions PR, the positions of the radiation source 2 and the radiographic image detector 3 after adjustment. The radiography control means 20 associates the actual-past-radiography positions PR with information about the subject S, such as the name and the height of the subject S, and stores the actual-past-radiography positions PR in an actual-past-radiography position database RDB. Further, the radiography control means 20 stores information about the operator UI (radiographer) who performed radiography and the order of radiography performed by the operator UI, associating the information with the actual-past-radiography positions PR.

Figure 3:
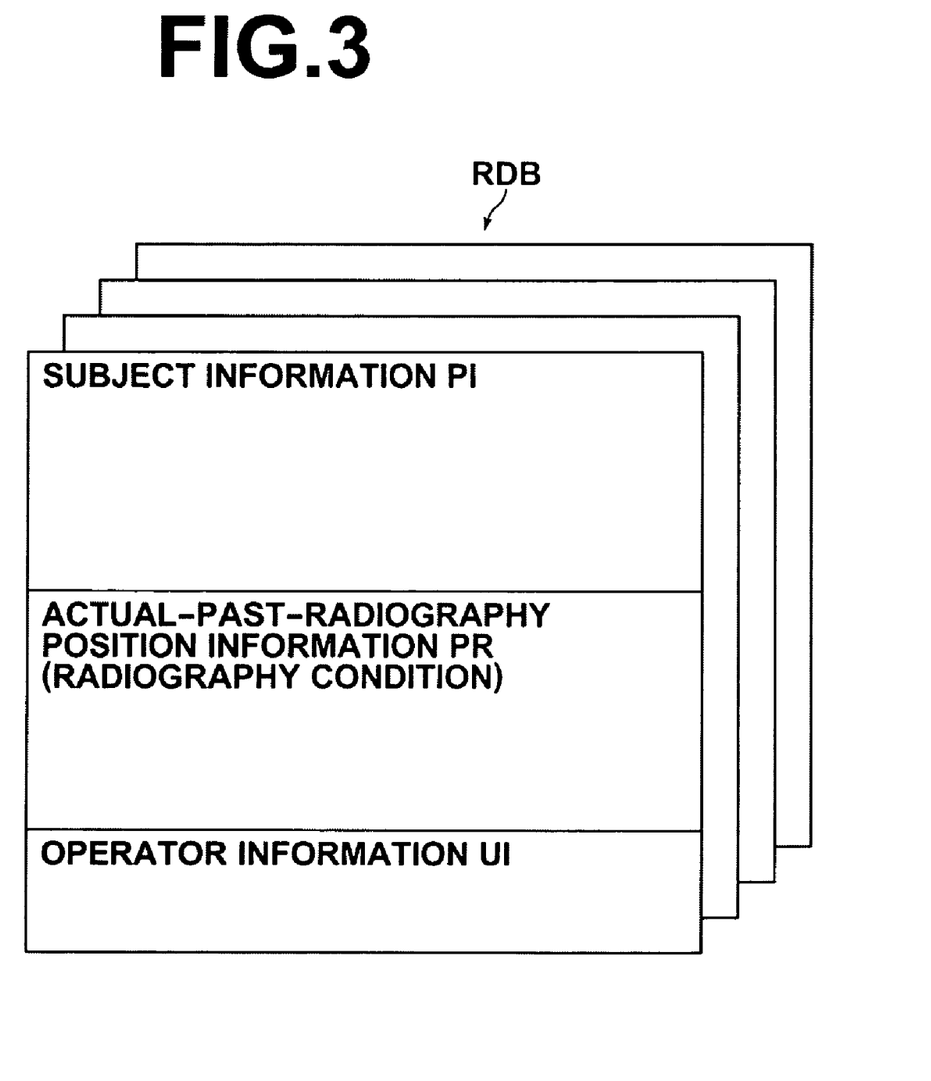
FIG. 3 is a schematic diagram illustrating an example of data structure of an actual-past-radiography position database illustrated in FIG. 2.

Therefore, the actual-past-radiography position database RDB stores, as actual-past-radiography positions PR, the position of the radiographic image detector 3 and the position of the radiation source 2 when radiography was actually performed. The positions are associated with the information PI about the subject S, and stored in the actual-past-radiography position database RDB. Specifically, as illustrated in FIG. 3, the actual-past-radiography position database RDB stores information about the subject (the name, the sex, the height, the weight or the like of the subject), the actual-past-radiography positions PR, and information about the operator UI (radiographer). These three kinds of information are correlated with each other, and stored. Further, the actual-past-radiography positions PR may be associated with an electronic clinical chart, and stored in the actual-past-radiography position database RDB. The electronic clinical chart includes information, such as a radiographic image, the condition of the disease, and a treatment history.

Further, the radiography control means 20 has a function of judging whether information about subject S to be radiographed (subject S who will be radiographed next, or the like) is present in the actual-past-radiography position database RDB. When the information about the subject S to be radiographed is present in the actual-past-radiography position database RDB because radiography was performed on the same subject S in the past, the radiography control means 20 outputs, at a display device 100, information that radiography was performed in the past. Further, the radiography control means 20 displays a question message or the like asking the operator UI whether radiography should be performed in the same radiography condition as the condition of the past radiography, and at the same position as the position of the past radiography. When the operator UI has input an instruction at an input means 50 to perform radiography based on the actual-past-radiography positions PR, the radiography control means 20 positions the radiation source 2 and the radiographic image detector 3 by using the actual-past-radiography positions PR associated with the information about the subject S, and radiography is performed.

As described above, when radiography of the subject S was performed in the past, and the past-actual-radiography positions PR are stored, if radiography is performed based on the stored past-actual-radiography positions PR, a plurality of radiographic images in the same angles as the angles of the past radiography can be obtained automatically. Therefore, when radiographic images are periodically obtained to diagnose the subject S (patient) by comparing the images with the past radiographic images, efficient radiography is possible.

When the radiation source 2 and the radiographic image detector 3 are positioned to perform radiography, the aid-information output means 30 outputs, as aid information AI, position adjustment amounts for adjusting the positions of the radiation source 2 and the radiographic image detector 3 from the standard positions PS stored in the standard position database SDB. The aid information AI is output based on the actual-past-radiography positions PR that are stored in the actual-past-radiography position database RDB and that are associated with the information PI about the subject. Specifically, the aid-information output means 30 includes an information classification means 31, an aid-information generation means 32, an aid-information retrieval means 33, and an aid database ADB.

The information classification means 31 classifies the actual-past-radiography positions PR stored in the actual-past-radiography position database RDB for each physical characteristic. For example, the information classification means 31 classifies the actual-past-radiography positions PR stored in the actual-past-radiography position database RDB for each physical characteristic, such as the height, the weight, and the sex of the subject. The aid-information generation means 32 generates, as the aid information AI, an average value or a mode value (a most frequent value) of the actual-past-radiography positions PR for each physical characteristic classified by the information classification means 31. Further, the aid-information generation means 32 stores, in the aid database ADB, a difference between the average value or the mode value and the standard positions PS (position adjust amounts) for each classification group of the physical characteristic. The aid-information generation means 32 periodically (regularly) updates the aid information AI to provide the aid information AI that reflects a new actual-past-radiography position.

When the information PI about the subject to be radiographed has been input, the aid-information retrieval means 33 retrieves the aid information AI to be provided for the operator UI. The aid information AI is retrieved from the aid database ADB based on the physical characteristic of the subject included in the information PI about the subject. Further, the aid-information retrieval means 33 outputs the retrieved aid information. Accordingly, even when radiography is performed on the subject S for the first time, expected adjustment amounts from the aforementioned standard positions PS are provided for the operator UI. Therefore, it is possible to reduce the time period for radiography.

Further, the aid-information output means 30 may have a function of calculating an average value of time periods for radiography by each operator UI, and outputting, as the aid information AI, the order of radiography performed by the operator UI who has a lowest average value of time periods. Accordingly, the operation for positioning may be performed with reference to the radiography operation (the order of radiography) performed by the operator UI who performed radiography in the shortest time period. Hence, more efficient radiography becomes possible. Further, the aid-information generation means 32 may generate the aid information AI for each physical characteristic as described above by using only the actual-past-radiography positions PR associated with the operator UI who performed radiography in the shortest time period.

Figure 4:
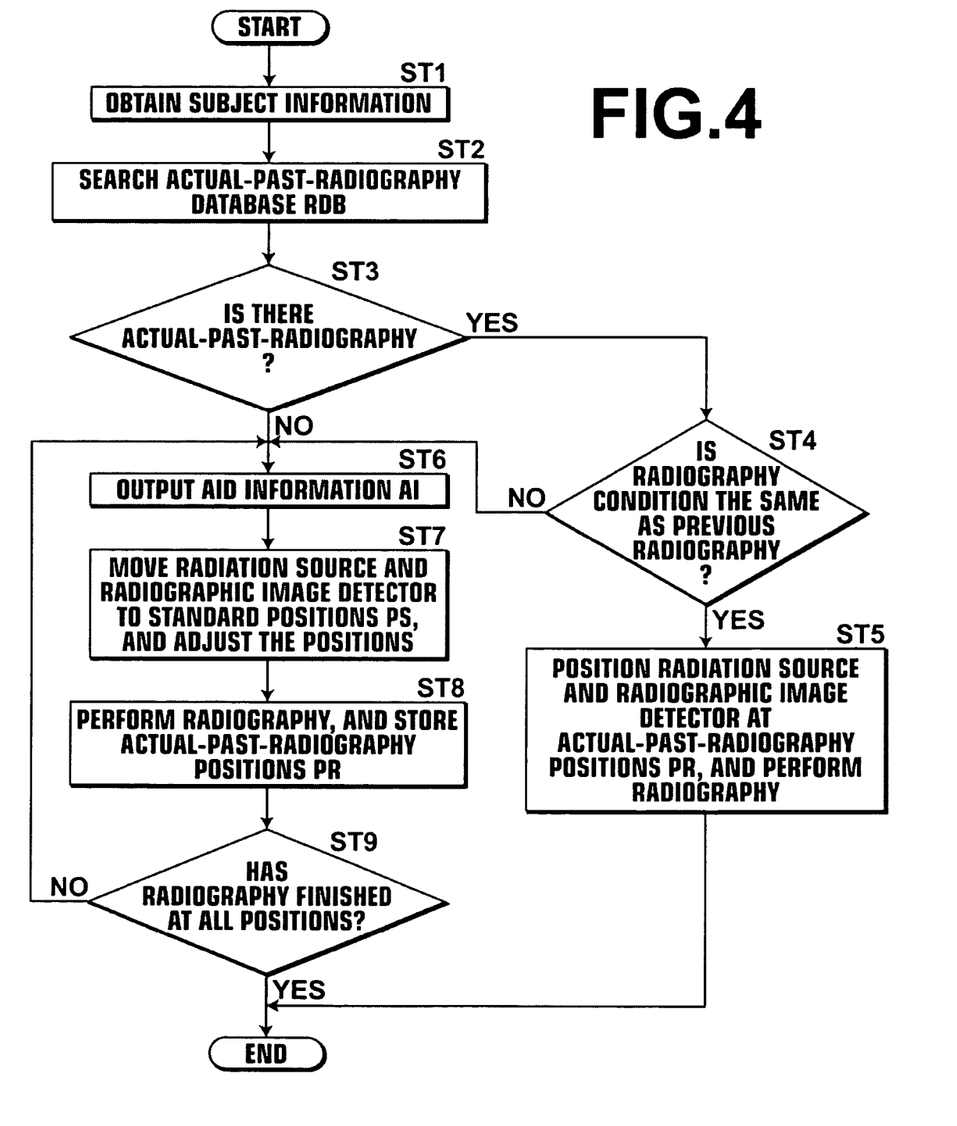
FIG. 4 is a flow chart illustrating an example of an operation by the radiographic image detection apparatus of the present invention.

FIG. 4 is a flow chart illustrating an example of an operation by the radiographic image detection apparatus of the present invention. With reference to FIGS. 1 thorough 4, the operation of the radiographic image detection apparatus will be described. First, subject information PI, such as the name of subject S, is input by operator UI by using an input means 50, for example (step ST1). Then, the radiography control means 20 searches the actual-past-radiography position database RDB to check whether radiography was performed on the same subject S in the past (step ST2).

If the subject information PI about the subject S is present in the actual-past-radiography position database RDB (step ST3), judgment is made as to whether the radiography condition is the same as the past radiography condition (step ST4). If it is judged that the radiography condition is the same as the past radiography condition, the radiation source 2 and the radiographic image detector 3 are positioned by using the actual-past-radiography positions PR stored in the actual-past-radiography position database RDB, and a predetermined number of times of radiography is performed (step ST5).

If the subject information PI about the subject S is not present in the actual-past-radiography position database RDB, that means radiography on the same subject S was not performed in the past (step ST3), the aid-information output means 30 searches the aid database ADB to retrieve data that is appropriate for the subject S, and outputs the retrieved data as the aid information AI (step ST6, please refer to FIG. 4). After the radiography control means 20 has positioned the radiation source 2 and the radiographic image detector 3 at standard positions PS, the operator UI adjusts, based on the aid information AI, the positions of the radiation source 2 and the radiographic image detector 3 from the standard positions PS to positions that are appropriate for the physique of the subject S (step ST7).

After then, radiation is output from the radiation source 2 to the subject S, and a radiographic image is obtained. At this time, the radiography control means 20 stores, as the actual-past-radiography positions PR, the positions of the radiation source 2 and the radiographic image detector 3 after adjustment of the positions by the operator UI in the actual-past-radiography position database RDB (step ST8). The output of the aid information AI, the adjustment of positions, radiography, and storage of data in the actual-past-radiography position database RDB, as described above, are repeated the same number of times as a predetermined number of times of radiography (steps ST6 through ST9).

As described in each of the embodiments of the present invention, the radiographic image detection apparatus of the present invention includes the radiation source 2 that outputs radiation to the subject S, the radiographic image detector 3 that detects, as a radiographic image, the radiation that has been output from the radiation source S to the subject S and that has passed through the subject S, the detector movement means 11 that moves the position of the radiographic image detector 3, the radiation-source movement means 12 that moves the position of the radiation source 2, the standard position database SDB that stores a predetermined position of the radiographic image detector 3 and a predetermined position of the radiation source 2 when radiographic images are obtained by changing the position of the radiographic image detector 3 and the position of the radiation source 2, the actual-past-radiography position database RDB that stores the position of the radiographic image detector 3 and the position of the radiation source 2 when radiography was performed at positions that are different from the positions stored in the standard position database SDB, associating the position of the radiographic image detector 3 and the position of the radiation sources 2 with information PI about the subject S, and the aid-information output means 30 that outputs, as aid information, position adjustment amounts for adjusting the positions of the radiation source 2 and the radiographic image detector 3 from the standard positions PS stored in the standard position database SDB when the radiation source 2 and the radiographic image detector 3 are positioned to perform radiography. The aid information AI is output based on the actual-past-radiography positions PR that are stored in the actual-past-radiography position database and that are associated with the information about the subject. Therefore, even when radiography is performed on a subject the position data of which is not recorded in the actual-past-radiography position database RDB, it is possible to provide the aid information AI that can be used as an index for positioning the radiation source 2 and the radiographic image detector 3 for the operator UI. Hence, it is possible to position the radiation source 2 and the radiographic image detector 3 in a short time period, and efficient radiography can be performed.

Further, as illustrated in FIG. 2, when the information PI about the subject S is a physical characteristic of the subject S, and the aid-information output means 30 includes the information classification means 31 for classifying the actual-past-radiography positions PR stored in the actual-past-radiography position database RDB for each physical characteristic of the subject, and the aid-information generation means 32 for generating, as the aid information AI, an average value or a mode value of the actual-past-radiography positions for each physical characteristic classified by the information classification means 31, and the aid-information retrieval means 33 for retrieving the aid information AI about a classification group to which the subject to be radiographed belongs from a plurality of sets of aid information generated by the aid-information generation means 32, and outputs the retrieved aid information, useful aid information that is appropriate for the physique of the subject can be provided for the operator UI.

Further, as illustrated in FIG. 3, when the actual-past-radiography position database RDB stores information about the operator UI who performed radiography and the order of radiography performed by the operator UI, associating the information about the operator UI and the order of radiography with the actual-past-radiography positions PR, and the aid-information output means 30 calculates an average value of time periods for radiography by each operator UI, and outputs, as the aid information AI, the order of radiography performed by the operator UI who has a lowest average value of time periods, the positioning operation can be performed with reference to the radiography operation performed by the operator UI who performed radiography in the shortest time period. Therefore, efficient radiography is possible.

Further, when the radiographic image detection apparatus 1 further includes the radiography control means 20 that controls the detector movement means 11 and the radiation-source movement means 12 so that the radiation source 2 and the radiographic image detector 3 are positioned as indicated by the actual-past-radiography positions PR of the subject S to be radiographed when the actual-past-radiography-positions PR of the subject S to be radiographed are stored in the actual-past-radiography position database RDB, if the actual-past-radiography positions PR of the subject S to be radiographed are stored in the actual-past-radiography position database RDB because radiography was performed on the subject S in the past, it is possible to position the radiation source 2 and the radiographic image detector 3 at the same positions as the past radiography stored in the actual-past-radiography position database RDB. Therefore, efficient radiography is possible so that the obtained radiographic image is compared with the radiographic image obtained in the past to diagnose the patient by using the images.

The embodiments of the present invention are not limited to the aforementioned embodiments. For example, in FIG. 1, a case in which the radiographic image detection apparatus 1 is a radiographic CT apparatus is illustrated. However, it is not necessary that the radiographic image detection 1 is the radiographic CT apparatus as long as the positions of the radiation source 2 and the radiographic image detector 3 can be moved. For example, the present invention may be applied to a standing-position-type radiographic image detection apparatus for performing so-called longitudinal radiography, a radiographic image detection apparatus using a so-called phase contrast method, a mammography apparatus and the like.

Further, in the aforementioned embodiments, the position adjustment amount from the standard position PS is output as the aid information AI. Alternatively, the radiography control means 20 may output a question message or the like to ask the operator UI whether the positions of the radiation source 2 and the radiographic image detector 3 should be moved to the positions represented by the aid information AI. Further, the radiography control means 20 may control, based on an input by the operator UI, so that the positions of the radiation source 2 and the radiographic image detector 3 are automatically moved to the positions represented by the aid information.

What is claimed is:

1. A radiographic image detection apparatus comprising:
   a radiation source that outputs radiation to a subject;
   a radiographic image detector that detects, as a radiographic image, the radiation that has been output from the radiation source to the subject and that has passed through the subject;
   a detector movement means that moves the position of the radiographic image detector;
   a radiation-source movement means that moves the position of the radiation source;
   a standard position database that stores, in advance, a standard position of the radiographic image detector and a standard position of the radiation source for obtaining the radiographic image by changing the position of the radiographic image detector and the position of the radiation source;
   an actual-past-radiography position database that stores, as actual-past-radiography positions, the position of the radiographic image detector and the position of the radiation source when radiography was actually performed, associating the position of the radiographic image detector and the position of the radiation source with information about the subject; and
   an aid-information output means that outputs, as aid information, position adjustment amounts for adjusting the positions of the radiation source and the radiographic image detector from the standard positions stored in the standard position database when the radiation source and the radiographic image detector are positioned to perform radiography, wherein the aid information is output based on the actual-past-radiography positions that are stored in the actual-past-radiography position database and that are associated with the information about the subject.

2. A radiographic image detection apparatus, as defined in claim 1, wherein the information about the subject is a physical characteristic of the subject, and wherein the aid-information output means includes an information classification means, an aid-information generation means, and an aid-information retrieval means, and wherein the information classification means classifies the actual-past-radiography positions stored in the actual-past-radiography position database for each physical characteristic of the subject, and wherein the aid-information generation means generates, as the aid information, an average value or a mode value of the actual-past-radiography positions for each physical characteristic classified by the information classification means, and wherein the aid-information retrieval means retrieves the aid information about a classification group to which the subject to be radiographed belongs from a plurality of sets of aid information generated by the aid-information generation means, and outputs the retrieved aid information.

3. A radiographic image detection apparatus, as defined in claim 1, wherein the actual-past-radiography position database stores information about an operator who performed radiography and the order of radiography performed by the operator, associating the information about the operator and the order of radiography with the actual-past-radiography positions, and wherein the aid-information output means has a function of calculating an average value of time periods for radiography by each operator, and outputting, as the aid information, the order of radiography performed by the operator who has a lowest average value of time periods for radiography.

4. A radiographic image detection apparatus, as defined in claim 1, wherein the actual-past-radiography positions include at least one of the position or the angle of the radiation source, the collimator rotation angle or the irradiation field of the irradiation source, and the position or the angle of the radiographic image detector.

5. A radiographic image detection apparatus, as defined in claim 1, further comprising a radiography control means that controls the detector movement means and the radiation-source movement means so that the radiation source and the radiographic image detector are positioned as indicated by the actual-past-radiography-positions of the subject to be radiographed when the actual-past-radiography-positions of the subject to be radiographed are stored in the actual-past-radiography position database.

* * * * *